(12) United States Patent
Hamersky et al.

(10) Patent No.: US 6,417,139 B2
(45) Date of Patent: Jul. 9, 2002

(54) COMPOSITIONS AND METHODS FOR CONTROLLING PLANT AND FLOWER MOISTURE TRANSPIRATION RATES

(75) Inventors: Mark William Hamersky, Hamilton; Steven Daryl Smith, Fairfield, both of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/759,386

(22) Filed: Jan. 12, 2001

Related U.S. Application Data

(60) Provisional application No. 60/176,276, filed on Jan. 14, 2000.

(51) Int. Cl.$^7$ ................................................. A01N 3/02
(52) U.S. Cl. ........................................ 504/114; 504/115
(58) Field of Search .................................. 504/114, 115

(56) References Cited

U.S. PATENT DOCUMENTS

| | | |
|---|---|---|
| 3,157,964 A | 11/1964 | Ferguson et al. |
| 4,094,845 A | 6/1978 | DeLong |
| 4,229,433 A | 10/1980 | Shigematsu et al. |
| 5,066,594 A | 11/1991 | DeBonte et al. |
| 5,201,925 A | 4/1993 | Itzel et al. |
| 5,343,653 A | 9/1994 | Itzel et al. |
| 5,489,569 A | 2/1996 | Bryant et al. |
| 5,500,403 A * | 3/1996 | Shafer et al. ............... 504/115 |
| 5,525,575 A | 6/1996 | Chamberlain |
| 5,529,975 A | 6/1996 | Chamberlain |
| 5,591,701 A | 1/1997 | Thomas |
| 5,635,443 A | 6/1997 | Lesenko |
| 5,679,617 A | 10/1997 | Hanafusa et al. |
| 5,747,416 A | 5/1998 | McArdle |
| 5,789,371 A | 8/1998 | Tracy et al. |
| 6,063,392 A | 5/2000 | Kloczko et al. |
| 6,103,253 A | 8/2000 | Hoffmann et al. |
| 6,110,451 A | 8/2000 | Matz et al. |

* cited by examiner

*Primary Examiner*—S. Mark Clardy
(74) *Attorney, Agent, or Firm*—Richard S. Echler; Bart S. Hersko

(57) ABSTRACT

The present invention relates to compositions for controlling plant and flower moisture transpiration and thereby extending the period of time in which cut flowers can be displayed before senescence produces a flower which has exceeded its aesthetic value. The compositions of the present invention comprise:

a) from about 0.1% to about 20% by weight, of a homopolymer or copolymer comprising monomers having the formula:

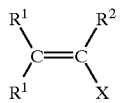

wherein each $R^1$ is independently hydrogen, $C_1$–$C_{12}$ alkyl, $C_1$–$C_{12}$ alkoxy, phenyl, substituted phenyl, benzyl, substituted benzyl, carbocyclic, heterocyclic, and mixtures thereof; $R^2$ is hydrogen, halogen, $C_1$–$C_{12}$ alkyl, $C_1$–$C_{12}$ alkoxy, phenyl, substituted phenyl, benzyl, substituted benzyl, carbocyclic, heterocyclic, and mixtures thereof; X is hydrogen, hydroxyl, halogen, —$(CH_2)_m CH_2OH$, —$(CH_2)_m COR$, —$(CH_2)_m CH_2OCOR'$, wherein R is —OR', —$N(R')_2$, —$(CH_2)_n N(R'')_2$, and mixtures thereof; each R' is independently hydrogen, $C_1$–$C_8$ alkyl, $C_2$–$C_8$ hydroxyalkyl, —$(CH_2)_n N(R'')_2$, and mixtures thereof; wherein R" is independently hydrogen, $C_1$–$C_4$ alkyl, and mixtures thereof; the index m is from 0 to 6, the index n is from 2 to 6;

b) from about 0.01% to about 5% by weight, of a surfactant; and c) the balance carriers and adjunct ingredients.

20 Claims, No Drawings

COMPOSITIONS AND METHODS FOR CONTROLLING PLANT AND FLOWER MOISTURE TRANSPIRATION RATES

This Application claims priority to U.S. Provisional patent application Ser. No. 60/176,276 filed Jan. 14, 2000.

FIELD OF THE INVENTION

The present invention relates to compositions for controlling plant and flower moisture transpiration rates and thereby providing a means for extending the time in which plants and cut flowers can be utilized in aesthetic displays or floral arrangements.

BACKGROUND OF THE INVENTION

Flowers have been inextricably linked to human culture since antiquity. Flowers have come to represent various aspects of life and to represent various facets of the human condition. As symbols of our society they speak directly. Flowers are never out of place regardless of the circumstances, inter alia, births, funerals, weddings, memorials.

Humans have cultivated and propagated flowers solely for their aesthetic value since most flowers are inedible. Incunabula describe various techniques for cutting and preserving flowers, inter alia, oriental flower varnishing, dipping blossoms into waxes or wax-like solutions. Contemporary practices include fashioning artificial flowers and blossoms from synthetic material, most notably polymers. However, all of these methods for preserving flowers, or attempts at flower imitation, fails to reproduce or replace the freshness of newly cut flowers.

The prior art has attempted to provide methods of preserving cut flowers in a fresh state, but the means are inadequate to provide flowers in a nearly original state for an enhanced period of time, for example, two to five times the expected period of use.

There is, therefore, a long felt need to provide the consumer or the grower of flowers which are to be cut and displayed for aesthetic purposes, with a system with significantly extends the duration in which the cut flowers maintain their original appearance.

SUMMARY OF THE INVENTION

The present invention meets the aforementioned needs in that it has been surprisingly discovered that cut flowers can be preserved in a nearly original state for an extended period of time, in fact, in some instances a period which eclipses their aesthetic utility. It has been surprisingly discovered that by controlling the plant and flower moisture transpiration rates flowers can be cut and displayed without the pejorative effects of natural demise (senescence), inter alia, wilting (epinasty) or loss of petals, browning or discoloration of flower parts. This post-harvest viability can be suitably established by effectively applying a moisture vapor barrier which itself does not contribute to diminished plant aesthetic value, i.e., petal burning or browning.

Flowers are ubiquitous in that they can adapt to environmental or ecological stresses. For example, during times of drought or other circumstances of water deprivation, flowers regulate their growth thereby attenuating the effects which moisture deprivation stress has on their viability. This ability to self regulate their growth cycle ameliorates many of the pejorative consequences of water deprivation on flower survival. Once flowers are cut during harvesting, the natural regulatory systems, inter alia, respiration, water regulation, are abated. It has been surprisingly discovered that an artificial level of viability can be maintained by applying a composition which controls the loss of plant tissue moisture via transpiration/evaporation.

The first aspect of the present invention relates to a composition for controlling plant and flower moisture transpiration, said composition comprising:

a) from about 0.1% to about 20% by weight, of a homopolymer of copolymer comprising monomers having the formula:

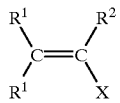

wherein each $R^1$ is independently hydrogen, $C_1$–$C_{12}$ alkyl, $C_1$–$C_{12}$ alkoxy, phenyl, substituted phenyl, benzyl, substituted benzyl, carbocyclic, heterocyclic, and mixtures thereof; $R^2$ is hydrogen, halogen, $C_1$–$C_{12}$ alkyl, $C_1$–$C_{12}$ alkoxy, phenyl, substituted phenyl, benzyl, substituted benzyl, carbocyclic, heterocyclic, and mixtures thereof; X is hydrogen, hydroxyl, halogen, —(CH$_2$)$_m$CH$_2$OH, —(CH$_2$)$_m$COR, —(CH$_2$)$_m$CH$_2$OCOR', wherein R is —OR', —N(R')$_2$, —(CH$_2$)$_n$N(R')$_2$, and mixtures thereof; each R' is independently hydrogen, $C_1$–$C_8$ alkyl, $C_2$–$C_8$ hydroxyalkyl, —(CH$_2$)$_n$N(R")$_2$, and mixtures thereof; wherein R" is independently hydrogen, $C_1$–$C_4$ alkyl, and mixtures thereof; the index m is from 0 to 6, the index n is from 2 to 6;

b) from about 0.01% to about 5% by weight, of a surfactant; and c) the balance carriers and adjunct ingredients.

The compositions of the present invention can be applied to the surface of cut plants or flowers by any means appropriate, for example, the flowers may be dipped into a solution, or the composition may be delivered via spray. The presence or the lack of a propellant to deliver said composition has no effect on the ability of the compositions to effectively and evenly coat the surface of the plant regardless of plant morphology.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (°C.) unless otherwise specified. All documents cited are in relevant part, incorporated herein by reference.

DETAILED DESCRIPTION OF THE INVENTION

The present invention relates to compositions for controlling plant and flower moisture transpiration rates and thereby providing a system for extending the time in which plants and cut flowers can be utilized in aesthetic displays or floral arrangements. The present invention is achieved by controlling the rate at which water is lost from the plant or cut flower via evaporation.

Without wishing to be limited by theory it has been found that control of the evaporation of water from cut flowers enhances the duration in which flowers appear in their pre-harvested, natural state. It has also been surprisingly discovered that a certain class of surfactant acts to evenly apply the moisture vapor barrier material (copolymer as described herein below) and does so without rupturing the plant cells thereby leading to browning of leaves and other aesthetic negatives.

For the purposes of the present invention the term "aesthetic utility" is defined herein as "the duration in which a flower retains its aesthetic appeal". The end of aesthetic appeal may differ between species of plant or flower, however, non-limiting examples of a property which may contribute wholly or severally to a loss of aesthetic appeal include browning of petals, loss of petals, drooping or down turn of blossoms, wilting, and shrinkage of plant mass together with collapse of plant tissue. In some instances, one manifestation of senescence may abate the usefulness of the flower, for example, the "browning" of petals may preclude the further use of a flower regardless of the lack of other conditions which tend to detract from the aesthetic quality of the cut flower.

The compositions of the present invention can be delivered to the exposed surface of the flower or plant by any suitable means. Non-limiting examples of delivery of the compositions include, spraying by means of aerosol, or pump, direct immersion, and variations which combine elements of immersion and spraying.

Moisture Transpiration Controlling Polymer

The first component of the present invention comprises a homopolymer or copolymer which when applied to the air-exposed surface of a cut plant or flower produces a barrier having a water vapor transfer rate capable of establishing a moisture equilibrium which attenuates the onset of senescence and extends the duration of aesthetic utility for said cut plant or flower.

For the purposes of the present invention the term "polymer" is herein defined as "an oligomer, homo-polymer, co-polymer, or mixtures thereof which satisfy the herein described requirements for establishing a moisture equilibrium in the cut flower or plant". The polymers of the present invention may comprise any polymeric material which satisfactorily regulates the water vapor transfer rate of the plant or flower to which it is applied.

In one embodiment of the present invention, the polymers are co-polymers which are formed from one or more "vinyl monomers" having the formula:

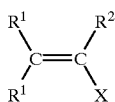

wherein each R' is independently hydrogen, $C_1$–$C_{12}$ alkyl, $C_1$–$C_{12}$ alkoxy, phenyl, substituted phenyl, benzyl, substituted benzyl, carbocyclic, heterocyclic, and mixtures thereof; $R^2$ is hydrogen, halogen, preferably chlorine or fluorine, $C_1$–$C_{12}$ alkyl, $C_1$–$C_{12}$ alkoxy, phenyl, substituted phenyl, benzyl, substituted benzyl, carbocyclic, heterocyclic, and mixtures thereof; X is hydrogen, hydroxyl, halogen, —$(CH_2)_m CH_2 OH$, —$(CH_2)_m COR$, $(CH_2)_m CH_2 OCOR'$ wherein R is —OR', —$N(R')_2$, —$(CH_2)_n N(R'')_2$, and mixtures thereof; each R' is independently hydrogen, $C_1$–$C_8$ alkyl, $C_2$–$C_8$ hydroxyalkyl, —$(CH_2)_n N(R'')_2$, and mixtures thereof; wherein R" is independently hydrogen, $C_1$–$C_4$ alkyl, and mixtures thereof; the index m is from 0 to 6, the index n is from 2 to 6. Non-limiting examples of preferred vinyl monomers include, ethylene, propylene, butylene, styrene, vinyl alcohol, crotyl alcohol, acrylic acid, styrylacetic acid, methacrylic acid, crotonic acid, 3,3-dimethyl-acrylic acid, methyl acrylate, ethyl acrylate, n-propyl acrylate, isopropyl acrylate, butyl acrylate, methyl methacrylate, ethyl methacrylate, n-propyl methacrylate, isopropyl methacrylate, butyl methacrylate, methyl 3,3-dimethyl-acrylate, ethyl 3,3-dimethyl-acrylate, n-propyl 3,3-dimethyl-acrylate, isopropyl 3,3-dimethyl-acrylate, butyl 3,3-dimethyl-acrylate, acrylamide, N-methyl acrylamide, N,N-dimethyl acrylamide, N-(aminoethyl) methyl acrylamide, vinyl acetate, and mixtures thereof.

In another embodiment of the present invention, the polymers are homopolymers which are formed from one or more "vinyl monomers" having the formula:

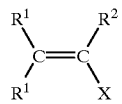

wherein $R^1$, $R^2$, and X are defined herein above.

In another embodiment of the present invention, a mixture of homopolymers anc copolymers are used.

One embodiment comprises polymers havi a water vapor transfer rate of less than 10 g-mm/m²-day, while other embodiments required a rate of 5 g-mm/m²-day. However, formulators may restrict the water vapor transfer rate to 2 g-mm/m²-day in preparing other suitable embodiments. Suitable means for determining water vapor transmission rates of polymers is by ASTM D1653 for a 0.02 inch (20 mill) film, ASTM E-96–66, Procedure E at 90% relative humidity and 100° F. for a 1 mm or 2 mm film, or TAPPI T 464 os-79 for a 2 mm film.

Copolymers of the present invention further have a glass transition temperature, $T_g$, greater than about 30° C., but other embodiments have $T_g$ values greater than about 40° C., yet other embodiments will have polymers with $T_g$ greater than about 60° C. The glass transition temperature, $T_g$, of a particular co-polymer can be approximated beforehand by the Fox formula (T. G. Fox, *Bull. Am. Phys. Soc.*, vol. 1 123 (1956) included herein by reference):

$$\frac{1}{T_{Co}} = \frac{W_1}{T_1} + \frac{W_2}{T_2} + \ldots \frac{W_n}{T_n}$$

wherein $W_1$ represents the weight portion of monomer 1, $W_2$ represents the weight portion of monomer 2, $T_1$ the glass transition temperature of the polymerized monomer 1 in °K., $T_2$ the glass transition temperature of the polymerized monomer 2 in °K., $T_{Co}$, the glass transition temperature of the copolymer in °K.

The formulator can readily establish whether a copolymer will satisfy the requirements of vapor transfer rate and glass transition temperature as set forth herein above. A plot of the glass transition temperature, $T_g$, expressed in °C. of the copolymer along the x axis (ordinate) versus the water vapor transfer rate expressed in g-mm/m²-day (measured or calculated) along the y axis (abscissa) preferably falls to the left of the line defined by the equation:

y=−0.068443x+10.

Points which fall to the right of said equation will have a permeability ineffective in establishing a suitable moisture barrier at a desirable glass transition temperature. Points which fall to the right of said equation may also produce films having no ability to form an aesthetically suitable surface. For example, too high of a glass transition temperature leads to hard and/or brittle films which may detract from the aesthetic qualities which are desirable. When formulating certain embodiments of the present invention, the water vapor transfer rate and glass transition temperature are adjusted such that the applied polymer produces a clear, colorless, translucent, and transparent film.

Another embodiment of the present invention relates to "crosslinkable vinyl monomers" having the formula:

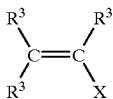

wherein X is the same as defined herein above; $R^3$ is $R^1$, $-(CH_2)_m CH_2OH$, $-(CH_2)_m CO_2R'$ wherein each R' is independently hydrogen, $C_1-C_8$ alkyl, and mixtures thereof; the index m is from 0 to 6. Non-limiting examples of "crosslinkable vinyl monomers" include maleic acid, fumaric acid, itaconic acid, citraconic acid, hydromuconic acid, and mixtures thereof.

The following are examples of non-limiting embodiments of the present invention:
 a) a composition comprising from about 0.1% by weight, of a polymer;
 b) a composition comprising from about 1% by weight, of a polymer;
 c) a composition comprising from about 2% by weight, of a polymer;
 d) a composition comprising from about 2.5% by weight, of a polymer;
 e) a composition comprising up to about 5%, by weight, of a polymer;
 f) a composition comprising up to about 7%, by weight, of a polymer;
 g) a composition comprising up to about 10%, by weight, of a polymer;
 h) a composition comprising up to about 20%, by weight, of a polymer.

The polymer can be obtained for use in any form, for example, as a dispersion in the reaction (polymerization) solvent, or the polymer can be provided as a solid. In one variation of the present invention some of carboxylic acid residues, acrylic acid, inter alia, which comprise the polymers of the present invention will be neutralized. For example, the following are non-limiting examples of the embodiments which relate to neutralization of the acid groups:
 a) a composition wherein from about 1% of said carboxylic acid residues are neutralized in said polymer;
 a) a composition wherein from about 5% of said carboxylic acid residues are neutralized in said polymer;
 a) a composition wherein from about 10% of said carboxylic acid residues are neutralized in said polymer;
 a) a composition wherein to about 100% of said carboxylic acid residues are neutralized in said polymer;
 a) a composition wherein to about 50% of said carboxylic acid residues are neutralized in said polymer;
 a) a composition wherein from about 20% of said carboxylic acid residues are neutralized in said polymer;
 a) a composition wherein from about 15% of said carboxylic acid residues are neutralized in said polymer;

Suitable means for neutralization includes the use of bases, non-limiting examples of which include alkaline metal hydroxides, inter alia, sodium hydroxide, alkaline earth metal hydroxides, inter alia, calcium hydroxide, ammonia, and mixtures thereof. The degree of neutralization typically depends upon the selected monomers which comprise the polymer and which properties must be adjusted to insure the application of an homogeneous film which achieves the required glass transition temperatures and vapor transmission rates described herein.

The first compositions comprise a polymer, in another embodiment a copolymer, which is solublized in a carrier. As described herein below, the typical and most convenient carrier is water or in another embodiment water together with one or more alcohol co-solvents. Some polymers which comprise one or more carboxylic acid monomers can be made water soluble or water dispersible by converting all or some of the carboxylic acid residues to carboxylic acid salts by treatment with base. It will be appreciated by the formulator that the water vapor transfer rates of the polymers will by related to the hydrophilicity of the polymers; the more hydrophilic a polymer the higher the water vapor transfer rate. Some formulators, for aesthetic purposes, may desire the polymers of the present invention, when applied to the plant surface, to form a clear, colorless, translucent, and transparent membrane. Therefore, it is preferable that the polymers of the present invention when utilizing this embodiment are delivered via the carrier solution such that evaporation of the carrier solution leads to formation of a homogeneous polymer layer rather than "clumping" due to differential spreading along the flower surface.

An example of a suitable copolymer comprises the reaction product obtained when polymerizing:
 i) from about 20% to about 60% by weight, of methyl methacrylate;
 ii) from about 20% to about 60% by weight, of butyl acrylate; and
 iii) from about 0.5% to about 20% by weight, of acrylic acid.

Another copolymer comprises the reaction product obtained when reacting:
 i) from about 40% to about 50% by weight, of methyl methacrylate;
 ii) from about 40% to about 50% by weight, of butyl acrylate; and
 iii) from about 5% to about 15% by weight, of acrylic acid.

A further example of a copolymer suitable for use in the present invention comprises:
 i) about 43% by weight, of methyl methacrylate;
 ii) about 47% by weight, of butyl acrylate; and
 iii) about 10% by weight, of acrylic acid.

Each of the above embodiments, neutralization of the acrylic acid residues can be achieved with a suitable base, for example, at least 5%, or in another case 10% of the acrylic acid residues.

Any suitable process can be used to form the compositions according to the present invention. However, it has been surprisingly discovered that the following process allows for the efficient formation of the polymeric solutions without phase separation. The process of the present invention comprises the steps of:
 a) dissolving a solid polymeric material free from solvents in the alcohol portion of the carrier;
 b) neutralizing acid residues to the desired level by adding dropwise an aqueous solution of base, preferably sodium hydroxide, more preferably 30% by weight sodium hydroxide;

c) adding at a rate of from 0.1% of the water which comprises the balance of the carrier to 10% of the water which comprises the balance of the carrier per minute; and d) adding the surfactant.

The process of the present invention, starting from a latex, comprises the steps of:

a) adding to an aqueous latex of a polymer comprising from about 25% to about 70% solids, an alcohol or other co-solvent to form a diluted latex;

b) neutralizing acid residues of the polymer which comprises said polymer to the desired level by adding dropwise an aqueous solution of base, preferably sodium hydroxide, more preferably 30% by weight sodium hydroxide;

c) adding at a rate of from 0.1% of the water which comprises the balance of the carrier to 10% of the water which comprises the balance of the carrier per minute; and d) adding the surfactant.

Surfactant

The compositions of the present invention comprise a surfactant. The amount of said surfactant is predicated on the desired properties of the final delivery which is modifyable by the formulator. In a broad embodiment the compositions of the present invention comprise from about 0.01% by weight of surfactant, however, other embodiments will comprise from about 0.05%, or from about 0.1%. The formulator may choose the upper limit of surfactant to be about 5%, but about 2%, and even about 0.5% by weight, of a surfactant is suitable in executing the desirable compositions and embodiments of the present invention. This range of from about 0.01% to about 5% gives the formulator an opportunity to adjust the final compositions. Amounts of surfactant below 0.01% and above 5% by weight, are outside the scope of the present invention. The suitable surfactants of the present invention are surfactants which are capable of evenly wetting the surface of plants and which do not cause browning or other adverse reactions to the plant surface.

One class of surfactants suitable for use in the present invention have the formula:

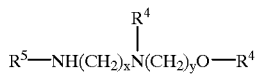

wherein $R^4$ is —$(CH_2)_zCO_2M$, —$(CH_2)_zSO_3M$, —$(CH_2)_zOSO_3M$, —$(CH_2)_zPO_3M$, and mixtures thereof; preferably —$(CH_2)_zCO_2M$, and mixtures thereof. The index z is from 1 to 10, preferably 2 to 4, more preferably 2 or 3. M is hydrogen or a salt forming cation, preferably sodium or potassium, more preferably sodium. The indices x and y are each independently an integer from 2 to 6; preferably 2 or 3 more preferably 2. In a preferred embodiment the indices x and y are equal to each other. $R^5$ is an acyl unit having the formula:

wherein $R^6$ and $R^8$ are each independently hydrogen, $C_1$–$C_4$ alkyl, and mixtures thereof; $R^7$ is $C_2$–$C_{12}$ alkylene; t is from 0 to 10; the indices w' and w'' are each independently from 0 to 14, w'+w''=at least 6.

In one embodiment $R^5$ has the formula:

wherein $R^4$ is —$(CH_2)_zCO_2M$, and mixtures thereof; the y is equal to 2 or 3; the index y is equal to the index z. The index w' is at least 6, in another embodiment from 8, more in still other embodiments from 10 to 14, and up to 12.

A non-limiting example of a surfactant according to the present invention is disodium lauroampho diacetate having the formula:

available ex Rhodia as Miranol® Ultra 32.

The surfactants suitable for use in the present invention are surfactants which do not cause browning of flower petals. A 0.01% by weight, aqueous solution of a linear alkyl benzene sulphonate (LAS) is sprayed onto a control flower. Preferably white carnations are selected as the control and test flower. The amount of flower browning which is present after 48 hours is taken as a set point. Browning of this amount will render a surfactant unsuitable for use as a surfactant according to the present invention. Preferably surfactants which provide no change in flower petal morphology or color are selected for use in the present compositions.

Carriers and Adjunct Ingredients

The polymers which comprise the first component of the present invention are suitably dissolved in a carrier which is effective in delivering the polymer as a homogeneous layer to the flower or plant surface. Non-limiting examples of carriers according to the present invention include water and an alcohol selected from the group consisting of methanol, ethanol, isopropanol, n-propanol, ethylene glycol, propylene glycol, and mixtures thereof; preferably a carrier comprising both water and an alcohol wherein the ratio of water to said alcohol is from about 99:1 to about 1:99.

The first component of the present invention may further comprise one or more adjunct ingredients. Preferred adjunct ingredients are selected from the group consisting of surfactants, fragrance raw materials, pro-fragrances, pro-accords, dye, colorants, and mixtures thereof. Suitable pro-fragrances and pro-accords are described in U.S. Pat. No. 5,919,752 Morelli et al., issued Jul. 6, 1999; U.S. Pat. No. 5,756,827 Sivik, issued May 26, 1998; U.S. Pat. No. 5,744,435 Hartman et al., issued Apr. 25, 1998; and U.S. Pat. No. 5,965,767 Sivik et al., issued Oct. 12, 1999 all of which are incorporated herein by reference.

The compositions of the present invention are not restricted to preserving cut flowers and plants but are also useful in extending the life of harvested fir trees, inter alia, for use as Christmas trees, or the cuttings taken from branches for use as adornment. Coniferous trees, typically, firs which are placed in the home as adornments during Christmas are subject to dehydration and are, therefore, prone to dropping their needles and becoming a fire hazard. The compositions of the present invention can be used to extend the life of fir trees which are harvested for holiday decorations. Palm fronds as well as ferns may also have their aesthetic life extended by the compositions of the present invention.

The following are non-liming examples of the compositions which comprise the present invention.

TABLE I

| Ingredients | weight % | | | |
|---|---|---|---|---|
| | 1 | 2 | 3 | 4 |
| Copolymer[1] | 2.5 | — | — | — |
| Copolymer[2] | — | 2.2 | — | — |
| Copolymer[3] | — | — | 2.9 | — |
| Copolymer[4] | — | — | — | 1.8 |
| Surfactant[5] | 0.1 | 0.1 | 0.1 | 0.1 |
| Preservative[6] | 0.0002 | 0.0002 | 0.0002 | 0.0002 |
| Carrier[7] | balance | balance | balance | balance |
| Percent acid residues neutralized | 10 | 10 | 10 | 12 |

[1] Reaction product of: i) about 43% by weight, of methyl methacrylate; ii) about 47% by weight, of butyl acrylate; and iii) about 10% by weight, of acrylic acid.
[2] Reaction product of: i) about 40% by weight, of methyl methacrylate; ii) about 47% by weight, of butyl acrylate; and iii) about 13% by weight, of acrylic acid.
[3] Reaction product of: i) about 43% by weight, of methyl methacrylate; ii) about 45% by weight, of butyl acrylate; and iii) about 12% by weight, of acrylic acid.
[4] Reaction product of: i) about 43% by weight, of methyl methacrylate; ii) about 43% by weight, of butyl acrylate; and iii) about 14% by weight, of acrylic acid.
[5] Disodium lauroampho diacetate available ex Rhodia as Miranol® Ultra 32.
[6] Kathon ICP/CG II.
[7] 80% distilled water, 20% SD-3A alcohol ex J. T. Baker.

What is claimed is:

1. A composition for controlling plant and flower moisture transpiration, said composition comprising:
   a) from about 0.1% to about 20% by weight, of a homopolymer or copolymer comprising monomers having the formula:

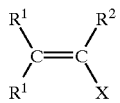

wherein each R' is independently hydrogen, $C_1$–$C_{12}$ alkyl, $C_1$–$C_{12}$ alkoxy, phenyl, substituted phenyl, benzyl, substituted benzyl, carbocyclic, heterocyclic, and mixtures thereof; $R^2$ is hydrogen, halogen, $C_1$–$C_{12}$ alkyl, $C_1$–$C_{12}$ alkoxy, phenyl, substituted phenyl, benzyl, substituted benzyl, carbocyclic, heterocyclic, and mixtures thereof; X is hydrogen, hydroxyl, halogen, —$(CH_2)_m CH_2OH$, —$(CH_2)_m COR$, —$(CH_2)_m CH_2OCOR'$, wherein R is —OR', —$N(R')_2$, —$(CH_2)_n N(R'')_2$, and mixtures thereof; each R' is independently hydrogen, $C_1$–$C_{18}$ alkyl, $C_2$–$C_8$ hydroxyalkyl, —$(CH_2)_n N(R'')_2$, and mixtures thereof; wherein R" is independently hydrogen, $C_1$–$C_4$ alkyl, and mixtures thereof; the index m is from 0 to 6, the index n is from 2 to 6;
   b) from about 0.01% to about 5% by weight, of a surfactant; and
   c) the balance carriers and adjunct ingredients.

2. A composition according to claim 1 wherein said homopolymer or copolymer comprises monomers selected from the group consisting of ethylene, propylene, butylene, styrene, vinyl alcohol, crotyl alcohol, acrylic acid, styrylacetic acid, methacrylic acid, crotonic acid, 3,3-dimethylacrylic acid, methyl acrylate, ethyl acrylate, n-propyl acrylate, isopropyl acrylate, butyl acrylate, methyl methacrylate, ethyl methacrylate, n-propyl methacrylate, isopropyl methacrylate, butyl methacrylate, methyl 3,3-dimethyl-acrylate, ethyl 3,3-dimethyl-acrylate, n-propyl 3,3-dimethylacrylate, isopropyl 3,3-dimethylacrylate, butyl 3,3-dimethyl-acrylate, acrylamide, N-methyl acrylamide, N,N-dimethyl acrylamide, N-(aminoethyl) methyl acrylamide, and mixtures thereof.

3. A composition according to claim 2 wherein said copolymer comprises:
   i) from about 20% to about 60% by weight, of methyl methacrylate;
   ii) from about 20% to about 60% by weight, of butyl acrylate; and
   iii) from about 0.5% to about 20% by weight, of acrylic acid.

4. A composition according to claim 3 wherein said copolymer comprises;
   i) from about 40% to about 50% by weight, of methyl methacrylate;
   ii) from about 40% to about 50% by weight, of butyl acrylate; and
   iii) from about 5% to about 15% by weight, of acrylic acid.

5. A composition according to claim 4 wherein said copolymer comprises;
   i) about 43% by weight, of methyl methacrylate;
   ii) about 47% by weight, of butyl acrylate; and
   iii) about 10% by weight, of acrylic acid.

6. A composition according to claim 3 wherein from about 1% to about 100% of said acrylic acid units are neutralized.

7. A composition according to claim 6 wherein from about 5% to about 20% of said acrylic acid units are neutralized.

8. A composition according to claim 1 comprising from about 1% to about 10% by weight, of said copolymer.

9. A composition according to claim 8 comprising to about 5% by weight, of said copolymer.

10. A composition according to claim 1 wherein said surfactant has the formula:

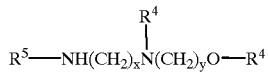

wherein $R^4$ is —$(CH_2)_z CO_2M$, —$(CH_2)_z SO_3M$, —$(CH_2)_z OSO_3M$, —$(CH_2)_z PO_3M$, and mixtures thereof; M is hydrogen or a salt forming cation; x and y are each independently an integer from 2 to 6; z is from 1 to 10; $R^5$ is an acyl unit having the formula:

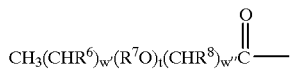

wherein $R^6$ and $R^8$ are each independently hydrogen, $C_1$–$C_4$ alkyl, and mixtures thereof; $R^7$ is $C_2$–$C_{12}$ alkylene; t is from 0 to 10; the indices w' and w" are each independently from 0 to 14, w'+w"=at least 6.

11. A composition according to claim 10 wherein said surfactant has the formula:

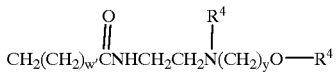

wherein $R^4$ is —$(CH_2)_z CO_2M$, and mixtures thereof; the index y is equal to the index z.

12. A composition according to claim 11 wherein said surfactant has the formula:

13. A composition according to claim 1 comprising from about 0.05% to about 2% by weight, of said surfactant.

14. A composition according to claim 13 comprising from about 0.1% to about 0.5% by weight, of said surfactant.

15. A composition according to claim 1 wherein said carrier comprises one or more solvents selected from the group consisting of water, methanol, ethanol, n-propanol, isopropanol, ethylene glycol, propylene glycol, and mixtures thereof.

16. A composition according to claim 15 wherein, said carrier comprises:
   i) from about 50% to about 90% by weight, of water; and
   ii) from about 50% to about 10% by weight, of one or more alcohols selected from methanol, ethanol, or isopropanol.

17. A composition for controlling plant and flower moisture transpiration, said system comprising:
   a) from about 2% to about 3% by weight, of a copolymer, said copolymer comprising:
      i) from about 40% to about 50% by weight, of methyl methacrylate;
      ii) from about 40% to about 50% by weight, of butyl acrylate; and
      iii) from about 5% to about 15% by weight, of acrylic acid;
   wherein at least 1% of said acrylic acid is neutralized;
   b) from about 0.05% to about 2% by weight, of a surfactant having the formula:

wherein $R^4$ is —$(CH_2)_zCO_2M$, —$(CH_2)_zSO_3M$, —$(CH_2)_zOSO_3M$, —$(CH_2)PO_3M$, and mixtures thereof; M is hydrogen or a salt forming cation; w' is an integer from 6 to 14; y is an integer from 2 to 6; z is from 1 to 10; and
   c) the balance a carrier comprising:
      i) from about 50% to about 90% by weight, of water; and
      ii) from about 50% to about 10% by weight, of one or more alcohols selected from methanol, ethanol, or isopropanol.

18. A composition according to claim 17 wherein said copolymer comprises;
   i) about 43% by weight, of methyl methacrylate;
   ii) about 47% by weight, of butyl acrylate; and
   iii) about 10% by weight, of acrylic acid
wherein about 10% of said acrylic acid is neutralized.

19. A composition according to claim 17 wherein said surfactant is disodium lauroamphodiacetate.

20. A method for enhancing the longevity of cut flowers comprising the step of applying to cut flowers an amount of a solution sufficient to cover the surface of said cut flowers, said solution comprising:
   a) from about 0.1% to about 20% by weight, of a homopolymer or copolymer comprising monomers having the formula:

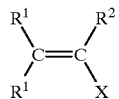

wherein each $R^1$ is independently hydrogen, $C_1$–$C_{12}$ alkyl, $C_1$–$C_{12}$ alkoxy, phenyl, substituted phenyl, benzyl, substituted benzyl, carbocyclic, heterocyclic, and mixtures thereof; $R^2$ is hydrogen, halogen, $C_1$–$C_{12}$ alkyl, $C_1$–$C_{12}$ alkoxy, phenyl, substituted phenyl, benzyl, substituted benzyl, carbocyclic, heterocyclic, and mixtures thereof; X is hydrogen, hydroxyl, halogen, —$(CH_2)_mCH_2OH$, —$(CH_2)_mCOR$, —$(CH_2)_mCH_2OCOR'$, wherein R is —OR', —$N(R')_2$, —$(CH_2)_nN(R'')_2$, and mixtures thereof; each R' is independently hydrogen, $C_1$–$C_8$ alkyl, $C_2$–$C_8$ hydroxyalkyl, —$(CH_2)_nN(R'')_2$, and mixtures thereof; wherein R" is independently hydrogen, $C_1$–$C_4$ alkyl, and mixtures thereof; the index m is from 0 to 6, the index n is from 2 to 6;
   b) from about 0.01% to about 5% by weight, of a surfactant; and
   c) the balance carriers and adjunct ingredients.

* * * * *

UNITED STATES PATENT AND TRADEMARK OFFICE
CERTIFICATE OF CORRECTION

PATENT NO. : 6,417,139 B2
DATED : July 9, 2002
INVENTOR(S) : Hamersky et al.

It is certified that error appears in the above-identified patent and that said Letters Patent is hereby corrected as shown below:

<u>Column 9,</u>
Line 42, "R'" should read -- $R^1$ --.
Line 52, "$C_1$-$C_{18}$" should read -- $C_1$-$C_8$ --.

Signed and Sealed this

Third Day of December, 2002

JAMES E. ROGAN
*Director of the United States Patent and Trademark Office*